US006566333B2

(12) United States Patent
Williams et al.

(10) Patent No.: US 6,566,333 B2
(45) Date of Patent: May 20, 2003

(54) OSTEOCLAST SECRETED CHEMOKINE AND USES THEREOF

(75) Inventors: John P. Williams, Lexington, KY (US); Jay M. McDonald, Birmingham, AL (US); Margaret A. McKenna, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/884,570

(22) Filed: Jun. 19, 2001

(65) Prior Publication Data

US 2002/0114779 A1 Aug. 22, 2002

Related U.S. Application Data

(60) Provisional application No. 60/212,271, filed on Jun. 19, 2000.

(51) Int. Cl.[7] ........................ A61K 38/00; A61K 38/19
(52) U.S. Cl. ............................ 514/12; 514/2; 424/85.1
(58) Field of Search ....................... 514/2, 12; 424/85.1

(56) References Cited

FOREIGN PATENT DOCUMENTS

KR 97065715 A * 10/1997

OTHER PUBLICATIONS

Yamada et al, p33, an endogenous target protein for arginine–specific ADP–ribosyltransferase in chicken polymorphonuclear leukocytes, is highly homologous to mim–1 protein (myb–induced myeloid protein–1). FEBS lett. 311:203–205, 1992.*

Swiss–Prot, Accession No. P08940, Jul. 15, 1999.*

Choi et al, A–Geneseq, Accession No. AAM52000, Mar. 15, 2002.*

* cited by examiner

*Primary Examiner*—Elizabeth Kemmerer
*Assistant Examiner*—Ruixiang Li
(74) *Attorney, Agent, or Firm*—Benjamin Aaron Adler

(57) ABSTRACT

The present invention demonstrates the biological function of a newly identified osteoclast-secreted protein. This protein, mim-1, has sequence homology with but is distinct from a previously identified neutrophil chemokine protein. Mim-1 may be a key signaling protein secreted by osteoclasts that regulates recruitment and/or differentiation of osteoblast and osteoclast precursor cells. This protein may also serve to maintain osteoclasts in a relatively inactive state prior to secretion. This mechanism is essential for regulating the mass and structural integrity of bone. This protein or an analog and/or antagonists of this protein will have potential therapeutic potential in the treatment of a variety of pathological bone diseases including osteoporosis and metastatic bone diseases.

2 Claims, 11 Drawing Sheets

| | | |
|---|---|---|
| 1 | YGCGYFGAPR | (SEQ ID NO.1) |
| 2 | LVCIHPIR | (SEQ ID NO.2) |
| 3 | FFHNGNSIDDGVQIR | (SEQ ID NO.3) |
| 4 | LLCIHPIR | (SEQ ID NO.4) |
| 5 | FFHNGNAIDDGVQISGSGYCVK | (SEQ ID NO.5) |
| 6 | VFPGIISHIHVENCDR | (SEQ ID NO.6) |
| 7 | GVDVICADGATVYAPFSGELSGPVK | (SEQ ID NO.7) |

MPALSLIALL SLVSTAFARQ WEVHPPQQQG RHWAQICSGN PFNRIRGCDR YGCGNYGASR
QGKGEKHKGV DVICTDGSIV YAPFSGQLSG PIFFFHNGNA IDDGVQISGS GYCVKLVCIH
PIRYHGQIQK GQQLGRMLPM QKVFPGIVSH IHVENCDQSD PTHLLRPIPD ISPPFPQQDA
HWAVVCAGNP TNEIRGCDKY GCGYFGAPRR NGKGEKHKGV DVICADGATV YAPFSGELSG
PVKFFHNGNA IDDGVQIRGS GFCVKLLCIH PIRYNGRISK GQVLGRMLPM QRVFPGIISH
IHVENCDRSD PTSNLERGKG ESEMEV (SEQ ID NO.8)

Fig. 3B

38 YGCGQYSAQR TQRHHP- GV DVLCSDGSVV YAPFTGKIVG QEKPYRNKNA INDGIRLSGR Lect2
51 YGCGNYGASR QGKGEKHKGV DVICTDGSIV YAPFSGQLSG PIRFFHNGNA IDDGVQISGS 110mimN
200 YGCGYFGAPR NGKGEKHKGV DVICADGATV YAPFSGELSG PVKFFHNGNA IDDGVQIRGS 260mimC 97 GFCVKIFYIK PIKYKGSIKK GEKLGTLLPL QKIYPGIQSH VHVENCDSSD PTAYL Lect2
111 GFCVKLLCIH PIRYNGRISK GQVLGRMLPM QRFVPGIISH IHVENCDRSD PTSNL 165 mim N
261 GYCVKLVCIH PIRYHGQIQK GQQLGRMLPM QKVFPGIVSH IHVENCDQSD PTHLL 315 mim C

Fig. 3C

OSTEOCLAST SECRETED CHEMOKINE AND USES THEREOF

CROSS-REFERENCE TO RELATED APPLICATION

This non-provisional patent application claims benefit of provisional patent application U.S. Serial No. 60/212,271, filed Jun. 19, 2000, now abandoned.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the fields of biochemical endocrinology and regulation of bone formation and degradation. More specifically, the present invention relates to the regulation of osteoblast function by the osteoclast-secreted chemokine-like protein mim-1 and uses thereof.

2. Description of the Related Art

Osteoclasts are multinucleated cells formed by fusion of precursors derived from pleuripotential hematopoietic stem cells (1) that circulate in the monocyte fraction (2, 3). Differentiation of the precursors into osteoclasts is a complex process that requires both M-CSF and RANKL (ODF, osteoclast differentiation factor; also known as TRANCE) (4, 5). The mechanism(s) by which osteoclastic precursors are recruited to an area of bone resorption, establish and differentiate into mature osteoclasts is a complex process that is still not fully understood.

Mature osteoclasts are terminally differentiated cells and while it is clear that M-CSF and RANKL are essential for differentiation of osteoclasts, additional osteoclast-inductive agents or synergistic effectors of RANKL are likely to be important in the development of active mature osteoclasts (6, 7). In fact, RANKL/TRANCE is not bone-specific since it was first cloned as a tumor necrosis factor (INF) related activation-induced cytokine (TRANCE) in T-cell hybridomas suggesting a potential role in immune function (8).

Communication via a variety of signaling molecules has long been proposed as a key component in the homeostatic signaling process between osteoclasts and osteoblasts (9, 10). Osteoclasts respond to numerous factors that are derived from bone or the bone microenvironment including, among others, IL-1, IL-6, TNFα and TGF-β, and osteoprotegrin (6, 7, 10–13). Under conditions of normal bone turnover, bone resorption is followed by new bone synthesis. The mechanisms regulating recruitment of osteoblast precursors into areas is recently degraded are poorly understood, but presumably involve a signaling pathway between osteoclasts and osteoblasts (14).

The prior art is deficient in methods of regulating the secretion of a chemokine-like protein expressed specifically by cells of hematopoietic origin, like osteoclasts, so as to manipulate a signaling pathway that may be involved in regulating recruitment of osteoblast precursor cells to areas of recent bone resorption. The present invention fulfills this long-standing need and desire in the art.

SUMMARY OF THE INVENTION

Mim-1 is a protein reported to be expressed specifically by cells of hematopoietic origin (15), which includes osteoclasts. Mim-1 is distinct from, but homologous with, the neutrophil chemokine protein, LECT2, and is an abundant protein in osteoclasts. In addition, mim-1 is secreted in a time dependent manner in vitro. Furthermore, secretion of mim-1 is stimulated in a PMA concentration dependent manner. Secretion of mim-1 precedes the largest increase in PMA stimulated bone resorption by isolated osteoclasts. Immunofluorescence microscopy demonstrated that both avian osteoclasts and human osteoclast-like cells express mim-1, but not mesenchymal stem cells (which includes osteoblast precursors). Mim-1 may be a key signaling protein secreted by osteoclasts that regulates recruitment and/or differentiation of osteoblast precursor cells, thereby providing an essential mechanism for regulating the mass and structural integrity of bone.

The present invention is drawn to methods of inducing recruitment and proliferation of osteoblasts and increased bone resorption by osteoclasts following secretion of mim-1. Generally, the mim-1 protein has the sequence of SEQ ID NO. 8 or a fragment thereof.

In another aspect of the present invention, there is provided methods of inducing bone resorption activity of osteoclasts, inducing recruitment and proliferation of osteoblasts, and inducing new bone synthesis in an individual by mim-1 protein. Generally, the mim-1 protein has the sequence of SEQ ID NO. 8 or a fragment thereof.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 3A, 3B, and 3C shows the sequence analysis of 35 kD osteoclast protein. Protein was tryptically digested from gel slices and peptides were resolved by HPLC (FIG. 3A) and sequenced. The full-length amino sequence of mim-1 is shown (FIG. 3B) and amino acids identified by sequence analysis are illustrated in bold. Some of the peptides had over-lapping sequence so that only five peptides are apparent. Repeat sequences from the N and C terminal ends of the protein are aligned with the homologous protein Lect2 (FIG. 3C). Conserved amino acids are illustrated in bold.

DETAILED DESCRIPTION OF THE INVENTION

Figure 1:
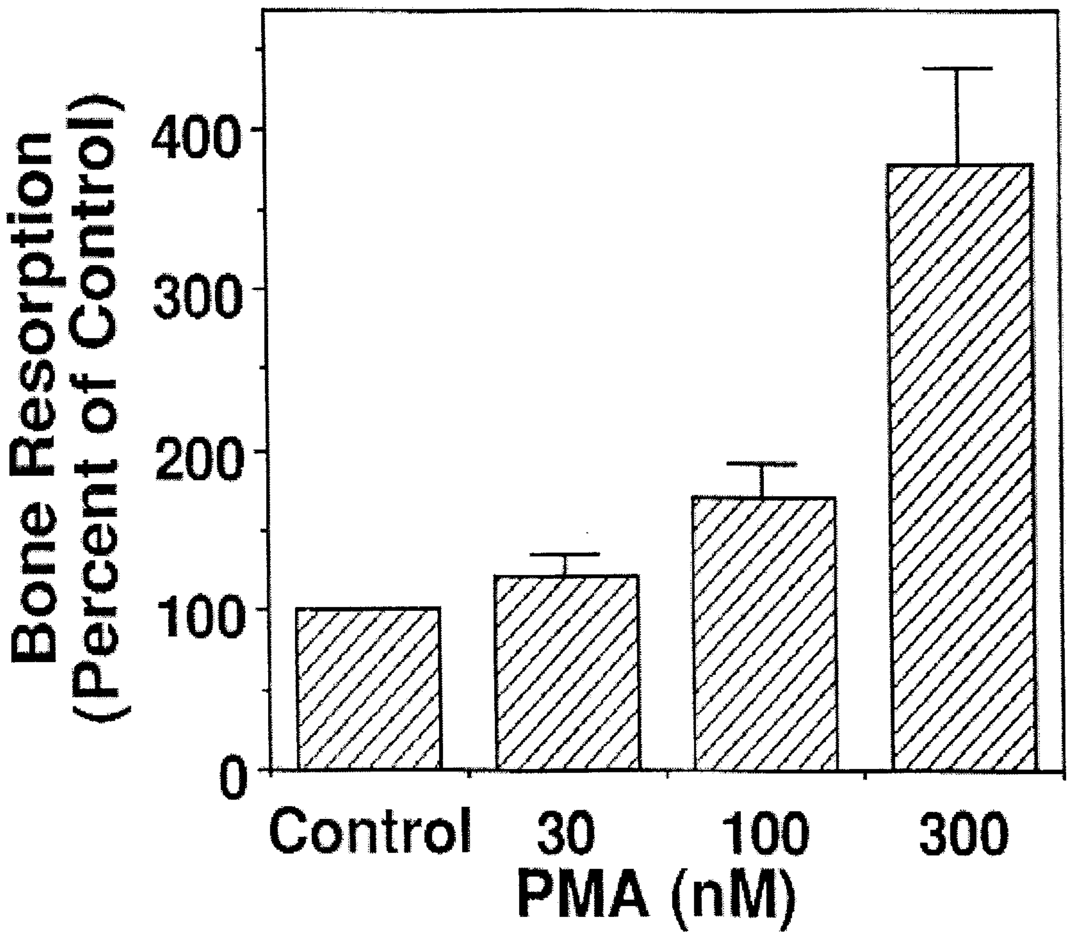
FIG. 1 shows the effect of PMA on osteoclastic bone resorption. Bone resorption assays using 150 μg labeled bone were cultured for four days in the presence of increasing concentrations of PMA. Resorption activity was quantified by measuring $^3$H proline released to the media. Data represent the mean+/−SEM of n=5 experiments each performed in quadruplicate.

The following abbreviations may be used herein: PMA, phorbol myristate acetate: Mim-1, myb induced myeloid protein-1; PBS, phosphate buffered saline; TRAP, tartrate resistant acid phosphatase; EGTA, ethylene glycol-bis($\beta$-aminoethylether) N,N',N'-tetraacetic acid; EDTA, ethylenedinitrilo tetraacetic acid; NaF, sodium fluoride; PMSF, phenylmethylsulfonylfluoride; SDS-PAGE, sodium dodecylsulfate-polyacrylamide gel electrophoresis; PVDF, polyvinylidine difluoride; BSA, bovine serum albumin.

Osteoclasts are terminally differentiated cells of hematopoietic origin. PMA stimulates bone resorption 4-fold with a simultaneous dose dependent increase in calmodulin protein levels. PMA treatment of osteoclasts also results in a dramatic decrease in a 35 kD protein in osteoclast lysates detected by Coomassie staining. The decrease in 35 kD protein correlates with increases in bone resorption. Peptide digests of the protein were analyzed by HPLC/MS/MS and provided sequence data for 7 peptides. Sequence analysis indicates that the protein is myb induced myeloid protein-1 precursor (mim-1 protein) based on sequencing 104 of 326 amino acids. Mim-1 is expressed specifically by cells of hematopoietic origin, has an internal repeat sequence of 136 amino acids, has no known function and is reported to be a secreted protein. Mim-1 is homologous with Lect2, a neutrophil chemokine, which also stimulates proliferation of osteoblasts. Western analysis demonstrated that the PMA dependent decrease in mim-1 in osteoclasts is due to the protein being secreted into culture media. Immunofluorescence studies demonstrate that mim-1 is localized with a cytoplasmic and perinuclear distribution, in both avian osteoclasts and human osteoclast-like cells. Expression and secretion of a chemokine-like protein suggests a possible, osteoclast derived, signaling pathway that may be involved in coordinating bone remodeling.

The present invention is drawn to methods of inducing bone resorption activity of osteoclasts, and inducing recruitment and differentiation of osteoblasts by mim-1 protein. Generally, the mim-1 protein has the sequence of SEQ ID NO. 8 or a fragment thereof.

In another aspect of the present invention, there is provided methods of inducing recruitment and differentiation of osteoblasts and increased bone resorption by osteoclasts following secretion of mim-1. Generally, the mim-1 protein has the sequence of SEQ ID NO. 8 or a fragment thereof.

The following examples are given for the purpose of illustrating various embodiments of the invention and are not meant to limit the present invention in any fashion:

EXAMPLE 1

Isolation and Culture of Osteoclasts

Avian osteoclasts (from egg-laying white Leghorn hens) were utilized because gram quantities of pure osteoclasts are readily obtained. Avian osteoclasts (>$10^7$ cells) were isolated as previously described (16). Laying hens on a limited calcium diet produce massive numbers of osteoclasts to meet the calcium requirement for eggshell production. The endosteum of such birds is >50% osteoclasts by mass. Medullary bone was scraped from the endosteum into calcium- and magnesium-free phosphate buffered saline (PBS) at 4° C. Cells were separated from matrix by washing through 100 $\mu$m nylon filters and sedimented through 70% newborn calf serum. Osteoclasts purified by density gradient sedimentation were ~75–90% viable. Following sedimentation, macrophages represent <2% of the cell mass. For experiments requiring homogeneous osteoclasts, the cells purified by serum sedimentation were then affinity purified by attachment to bone fragments and then resedimented 24 hrs later, eliminating essentially all but viable, bone-attached osteoclasts (17).

EXAMPLE 2

Human Osteoclast-Like Cell Differentiation

Human blood monocytes were isolated by plasma pheresis from healthy volunteers. Human blood monocytes (1x$10^5$ cells/well) were cultured in the presence of 90% confluent MG63 cells in Minimal Essential Media α containing 10% fetal bovine serum, $10^{-7}$ M dexamethasone, and $10^{-8}$ M 1, 25 dihydroxy vitamin $D_3$. Differentiation to TRAP positive cells was used as a marker for the osteoclast phenotype. In parallel experiments cells were plated at a similar density on 18x18 mm cover slips and immunostained for mim-1.

EXAMPLE 3

Preparation of Devitalized -[$^3$H]-Proline Labeled Bone

L-[$^3$H]-proline-labeled devitalized bone was used as substrate in the avian osteoclast resorption assay. This substrate has the advantages of reflecting removal of both the mineral and organic phases of bone, and is resistant to artifacts due to physicochemical exchange (e.g., media acidification (16)). Weanling rats (40–60 g) were injected with 1 mCi of L-[2,3,4,5-$^3$H]-proline, >100 Ci/mmol, on alternate days for 10 days. Rats were sacrificed on day 12 and the bone was recovered by dissection. After washing, the bone was dried in a desiccator at 42° C. for 7 days. Labeled 20–40 $\mu$m bone fragments were obtained by grinding the bone in a ball bearing mill and sieving to size.

EXAMPLE 4

Bone Resorption Assays

Osteoclasts were plated at 2–3x$10^3$ cells/well on 24 well plates with 100 $\mu$g of labeled 20–40 $\mu$m $^3$H labeled bone fragments. To avoid possible contamination due to fusing macrophages or growth of fibroblast/osteoblast cells, bone resorption was measured after 4 days. Osteoclasts rapidly (~4 hrs) attach to and begin to degrade the bone fragments, releasing label into the media. Bone degradation was determined by measuring label released to the media. Comparison of the $^3$H proline release and pit assays give comparable results (17, 18). The $^3$H proline assay is also resistant to pH-dependent artifacts and has less inter-assay variability than pit assays (17–19). Activity with 100 $\mu$g bone fragments is linear over 5–7 days (16).

EXAMPLE 5

Osteoclast Lysis and Western Analysis

Avian osteoclasts were washed with phosphate buffered saline (PBS) and lysed as previously described (20). The lysis buffer (Buffer A) is 50 mM Tris, pH 7.0, 250 mM sucrose, 1 mM EGTA, 1 mM EDTA, 1 mM ammonium molybdate, 50 mM NaF, 1 mM orthovanadate, 0.5 $\mu$M okadaic acid, 5 mM benzamidine, 0.1 mM PMSF, 0.05 mg/ml pepstatin, 0.06 mg/ml leupeptin, 0.018 trypsin inhibitor units of aprotinin/ml, 10% glycerol and 1% Triton X100. Cells were solubilized 1 hr with rotation and the Triton insoluble material removed by centrifugation at 15,000xg for 5 min at 4° C. Lysates (25 $\mu$g protein) were resolved on 10% SDS-PAGE. Protein was transferred under standard conditions (21) to PVDF membranes. Mim-1 was detected on Western analysis using a polyclonal antibody generated against a trpE-mim-1 fusion protein (15) (generously provided by Scott Ness, University of New Mexico) by enhanced chemiluminescence. Protein concentrations were determined by the Bio Rad DC assay (Bio Rad, Richmond, Calif.).

EXAMPLE 6

Reagents for Protein Sequencing

High quality water was prepared using a Millipore (Bedford, Mass.) Milli-Q reagent grade water system. HPLC grade acetonitrile was purchased from Burdick and Jackson (Muskegon, Wis.). Sequencing Grade trifluoroacetic acid (TFA) was purchased from Pierce (Rockford, Ill.). Reagent grade ammonium bicarbonate was purchased from Mallinckrodt (St. Louis, Mo.). Iodoacetic acid was purchased from Sigma (St. Louis, Mo.), and dithiothreitol was purchased from Aldrich (Milwaukee, Wis.). Sequencing grade modified trypsin was purchased from Promega (Madison, Wis.).

EXAMPLE 7

In-gel Reduction/Alkylation and Digestion

Separated proteins were reduced, alkylated, and digested in-gel using a procedure based on published methods (22, 23). Gel pieces were finely diced and de-stained by multiple 40 minute extractions with 200 mM $NH_4HCO_3$ in 50% acetonitrile at 30° C. Destained gel pieces were dried in a vacuum centrifuge, then rehydrated with 10 mM dithiothreitol and reduced for 1 hour at 56° C. After reduction, the proteins were alkylated with 100 mM iodoacetic acid for 30 minutes in the dark at room temperature. Reaction products were removed by rinsing twice with 200 mM $NH_4HCO_3$, followed by twice shrinking the gel with acetonitrile and re-swelling it with 200 mM $NH_4HCO_3$. The gel pieces were dried in a vacuum centrifuge and re-swelled with 50 $\mu$g/ml trypsin in 100 mM $NH_4HCO_3$ (prepared by mixing equal volumes of a stock solution of 100 $\mu$g/ml trypsin in 1 mM HCl with 200 mM $NH_4HCO_3$). The gel pieces were covered with 200 mM $NH_4HCO_3$ and incubated overnight at 30° C. The reaction was quenched with 2 $\mu$l of 10% TFA followed by removal of the supernatant. The gel pieces were twice extracted with 100 μl 0.1% TFA in 60% acetonitrile. The combined extracts and supernatant were taken to near dryness in a vacuum centrifuge and stored frozen until analyzed.

EXAMPLE 8

Microcapillary HPLC/MS/MS Analysis

Protein digests were analyzed using a custom built microcapillary HPLC coupled to a Finnigan MAT LCQ Quadrupole Ion Trap Mass Spectrometer (24). Separations were carried out using 150 μm (inner diameter) porous polymer monolithic columns (25). Data were generated using the Finnigan triple play data-dependent analysis, in which an ion identified in a full mass range scan is scanned at high resolution to determine its appearance mass and charge state and then fragmented to give a tandem (MS/MS) mass spectrum. Instrument parameters were: 210° C. heated metal capillary temperature, 1.10 kV spray voltage, and 35% relative collision energy. Spectra were collected with 2 microscans and a $5\times10^7$ automatic gain control target for full scans, 5 microscans and $1.5\times10^6$ automatic gain control target for zoom (high resolution) scans, and 8 microscans and $1\times10^7$ automatic gain control target for MS/MS scans. MS/MS spectra were searched against the OWL nonredundant database using the Sequest (26) program. Sequest results were confirmed by manually comparing observed and predicted fragmentation patterns for the identified peptides.

EXAMPLE 9

Mim-1 Immunofluorescence Microscopy

Osteoclasts were cultured on 18×18 glass cover slips with or without 20–40 μm bone fragments. Cells were washed with ice cold phosphate buffered saline (PBS), fixed in 3% formaldehyde and permeabilized with 100% methanol for 30 min at −20° C. Nonspecific binding was blocked with 1% BSA in PBS at 23° C. for 15 minutes. Mim-1 polyclonal antibody (rabbit serum) or nonimmune serum was diluted 1:1000 in blocking buffer and incubated on cover slips for 1 hour at 23° C. Cover slips were washed 4 times for 15 minutes each with PBS and blocked again with blocking buffer. Secondary antibody (FITC conjugated) was diluted 1:1000 and incubated on the cover slips for an hour at 23° C. in the dark. Cover slips were Hoescht stained (20 μg/ml) for 1 hour for nuclear localization. Cover slips were mounted in 0.1% phenylenediamine in 90% glycerol/PBS. Fluorescence microscopy was performed on a Leica Wetzler microscope attached to a Power MacIntosh computer running IP Lab 3.2 software.

EXAMPLE 10

Results

Figure 2:
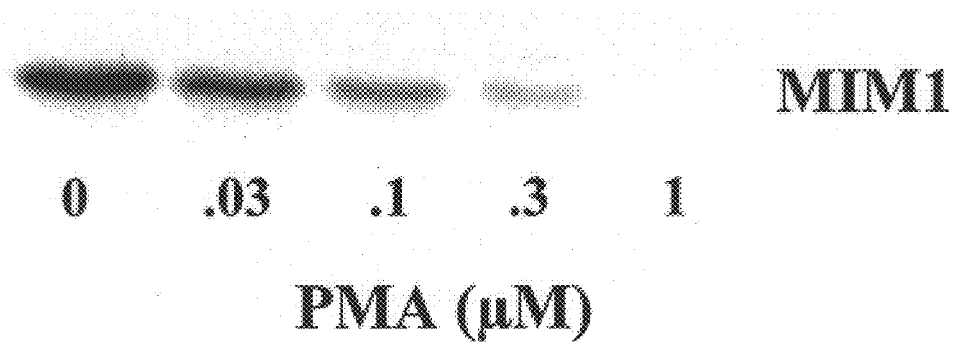
FIG. 2 shows the PMA concentration-dependent decrease in 35 kD osteoclast protein. Bone resorption assays using 150 μg labeled bone were cultured for four days in the presence of increasing concentrations of PMA as described in FIG. 1. Osteoclasts were washed with ice-cold phosphate buffered saline, lysed and 25 μg cell lysates resolved on 10% SDS-PAGE, stained, destained and gels dried. Dried gels were scanned on a UMAX S-12 scanner and the mim-1 protein band is shown. Data are representative of five experiments.

The phorbol ester, PMA, stimulated bone resorption by isolated osteoclasts 4-fold with a $K_{0.5}$ between 0.1 and 0.3 μM (FIG. 1). The PMA-concentration dependent increase in bone resorption was paralleled by a decrease in a 35 kD protein in osteoclast cell lysates as visualized on Coomassie stained gels (FIG. 2). This protein was the lowest molecular weight of three abundant proteins migrating between 35 and 40 kD on SDS-PAGE. The concentration of the 35 kD protein decreased dramatically in response to PMA while the relative abundance of the other two proteins in this region did not change with respect to Coomassie staining.

Figure 3A:
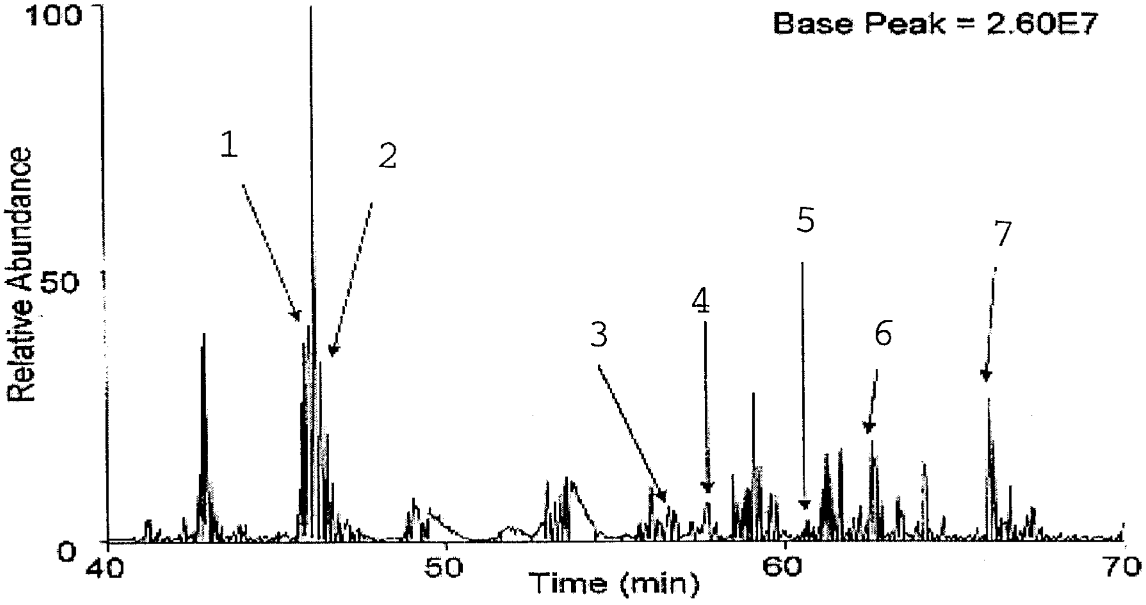

This protein, being one of the most abundant proteins in solubilized osteoclast lysates, was alkylated, reduced, tryptically digested and sequenced from excised gel slices and unambiguously identified as Chicken Myeloid Protein 1 (15, NCBI identifier P08940) or mim-1 (myb induced myeloid protein-1) as described above. Briefly, Coomassie stained bands were excised from gels post-transfer (reducing the number of potential background proteins) and tryptically digested (FIG. 3). Tryptic peptides were resolved by HPLC (FIG. 3A). Seven distinct peptides comprising 31.9% of the complete sequence were identified by tandem mass spectrometry (SEQ ID NO:1–7). One of the peptides identified included the amino acid at position 297, which is the site of a sequence conflict, and was found to be isoleucine rather than tyrosine. No other proteins were identified in the gel band containing the myeloid protein, with the exception of the regularly observed minor contaminant human keratin. Sequence obtained includes 104 amino acids (FIG. 3B) of the 326 amino acids in the full length sequence reported in original cloning and sequence paper (15). The sequenced peptides were illustrated in FIG. 3B in bold in the full-length sequence of mim-1 (SEQ ID NO: 8).

Examination of the sequence demonstrates that there is a repeat sequence of approximately 136 amino acids in each half of the protein joined by a 14 amino acid "linker". There is high sequence homology between the repeat sequences of mim-1 and the neutrophil chemokine protein, Lect2 (also known as chondromodulin II). The repeat sequences of mim-1 and Lect2 are aligned and illustrated in bold print in FIG. 3C (SEQ ID NO: 9–11). In this repeat structure there are 99 amino acids that are identical and most of the non-identical sites are conservative substitutions. This protein has no known function but was reported to be a secreted protein (15).

To determine the effects of PMA on osteoclast secretion of mim-1 and its relation to bone resorption, osteoclasts were cultured as described above in the absence of PMA and aliquots of media removed at the indicated times (FIG. 4) and the level of mim-1 determined by Western analysis. Levels of mim-1 increase throughout the 4 day time course. Osteoclasts were then treated with increasing concentrations of PMA, and bone resorption was measured (17, 27, 28). As bone resorption was stimulated (see FIG. 1), mim-1 decreased in the cell lysate (FIG. 5, left side, Lysates), and increased in the culture media (FIG. 5, right side, Media). It is also evident from these data that osteoclasts have a basal rate of secretion of mim-1 that is independent of PMA treatment.

Figure 6:
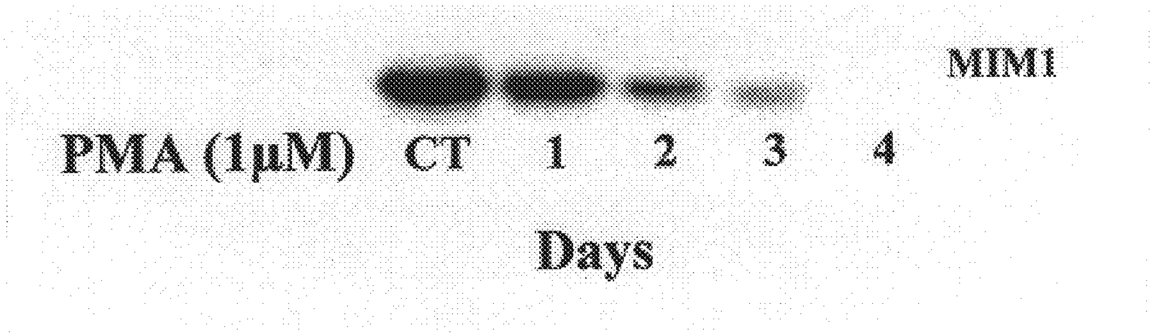
FIG. 6 shows the PMA time-dependent secretion of mim-1. Avian osteoclasts were cultured with bone (1 mg/well) for the indicated times in the presence of 1 $\mu$M PMA. Osteoclasts were washed with ice-cold phosphate buffered saline, lysed and 25 $\mu$g cell lysates resolved on 10% SDS-PAGE, transferred to PVDF membrane and probed with for mim-1 as described in the legend to FIG. 5. Data is representative of two separate experiments.

The decrease in mim-1 in osteoclast lysates in response to PMA treatment was rapid. Mim-1 was substantially reduced in cell lysates by 48 hours treatment with PMA (FIG. 6). The amount of mim-1 in cell lysates decreased by 25% after 24 hrs and 75% at 48 hrs of PMA treatment (FIG. 6A). Interestingly, this decrease in mim-1 preceded by a day the largest change in the time dependent increase in PMA stimulated bone resorption (FIG. 6B).

Figure 7A:
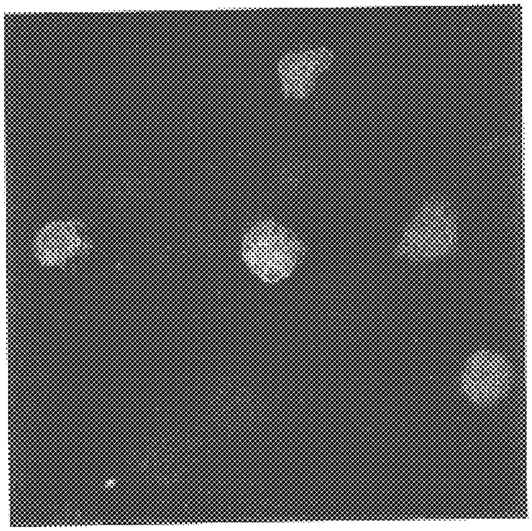
FIGS. 7A and 7B shows that human osteoclast-like cells express mim-1. Human blood monocytes ($5\times10^4$ cells) were cultured for 10 days in the presence of MG63 cells ($5\times10^5$ cells) in the presence of $10^{-8}$ M 1, 25 dihydroxy vitamin D3, and 25 ng/ml M-CSF. Cells were Hoescht stained for nuclear localization (blue color) and fluorescence labeling performed as described in the legend to FIG. 8 with mim-1 IgG (FIG. 7A) or nonimmune IgG (FIG. 7B). Data are representative of two experiments.

Mim-1 is expressed in bone marrow promyelocytes (18), and is secreted by osteoclasts (FIGS. 2, 4–6) and has been previously been reported to be localized within granules in granulocytes. Immunohistochemistry showed that mim-1 was present in both avian osteoclasts (data not shown) and human osteoclast-like cells derived from human blood monocytes (FIG. 7). Osteoclasts were Hoechst stained to show nuclei and mim-1 was localized by immunofluorescence microscopy with FITC labeled secondary antibody. In avian osteoclasts mim-1 fluorescence was localized in the cytosol and had a perinuclear pattern in osteoclasts. The fluorescence intensity decreased dramatically in response to PMA treatment, consistent with the observation that osteoclasts secrete mim-1 to the media. Mim-1 in PMA treated osteoclasts appeared to be within granules, similar to the distribution reported in promyelocytes (15). Mim-1 staining was specific since in both control and PMA treated osteoclasts fluorescence background with the nonimmune antibody was substantially lower than that with mim-1 antibody.

Figure 7B:
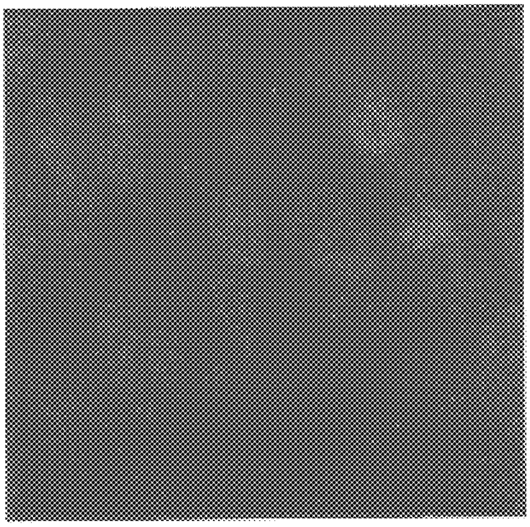

Mim-1 was present in the human osteoclast precursor cells (FIG. 7A) while cells treated with non-immune serum were negative (FIG. 7B). In these experiments the plane of focus was at the level of the blood monocytes which were above the MG63 cells. Consequently, the nuclei of the MG63 cells were out of the plane of focus and appeared dark blue rather than bright blue as in the monocytes. Numerous monocytes had begun to fuse as can be seen by the presence of bi-nucleated cells.

Mim-1 is also present in the mouse marrow macrophage differentiation model. In fact, mim-1 dramatically inhibited TRAP staining of osteoclast-like cells suggesting that mim-1 inhibits differentiation of these cells in the presence of M-CSF and soluble RANKL.

Figure 8:
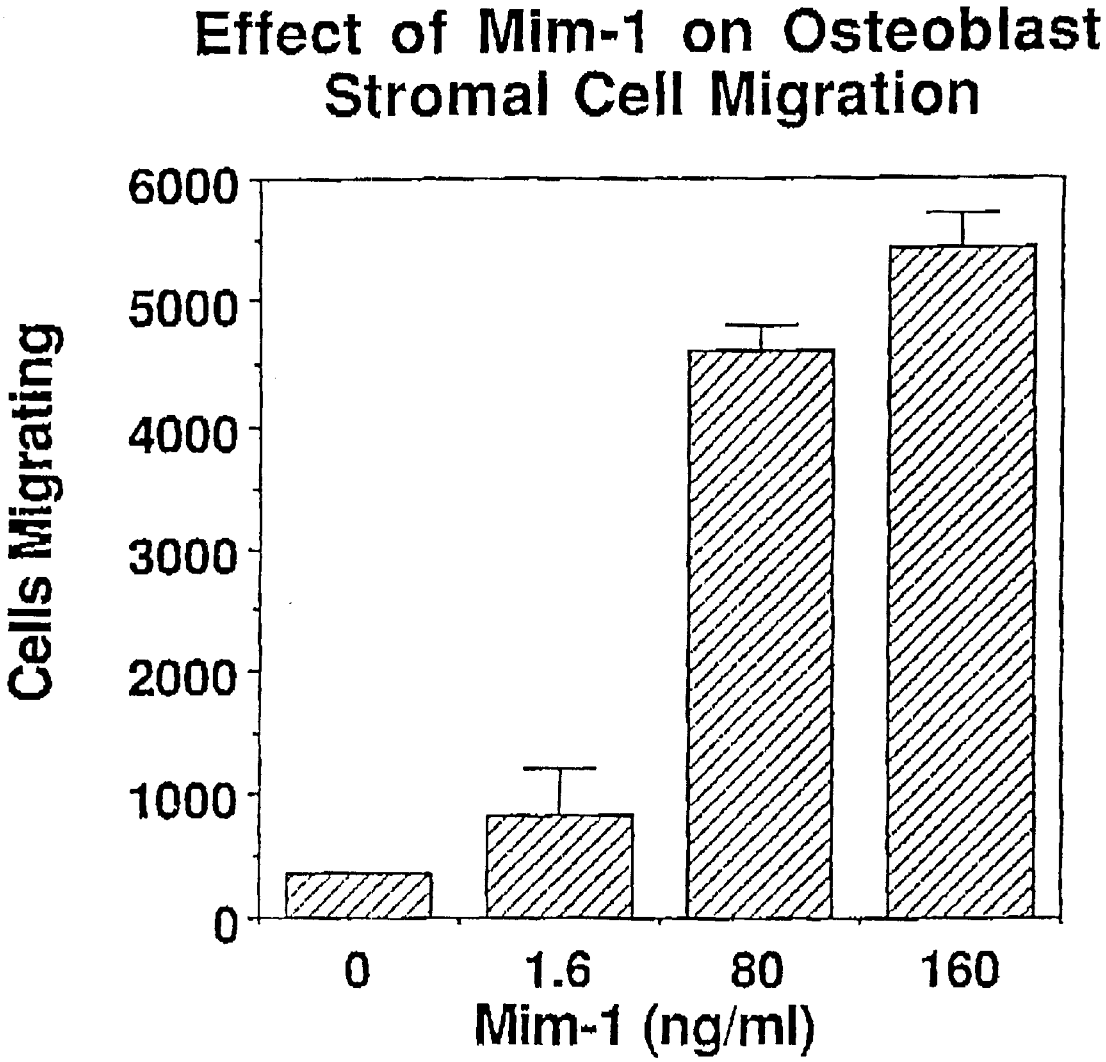
FIG. 8 shows mesenchymal stem cells (osteoblast precursors) migrate to mim-1 in a concentration dependent manner. Mesenchymal stem cells were loaded in the presence of 5 $\mu$M calcein in $\alpha$MEM, and the cells washed twice with media. Cells were plated at 10,000 cells/well in the upper well of Neuroprobe transwell plates. The concentration dependence of mim-1 in the transwell migration assay was determined with the indicated concentrations of mim-1 in the bottom wells. Cells were cultured for 4 hours at 37° C. in a humidified chamber with 5% $CO_2$. Remaining cells were scraped from the upper well and removed. Fluorescence was measured on a fluorescence plate reader which measures fluorescence in the bottom well and migration was determined by comparisons with a standard curve generated by serial dilutions of calcein loaded cells plated directly in the bottom wells. Data is from a single experiment performed in quadruplicate.

In order to examine whether mim-1 may regulate recruitment of osteoblast precursor cells, migration assays were performed on mesenchymal stem cells. As shown in FIG. 8, the stem cells migrated to mim-1 in a concentration dependent manner, suggesting that mim-1 may serve to attract osteoblast precursor cells to an area that is newly resorbed, thereby providing a mechanism for coordinating bone remodeling.

Figure 9:
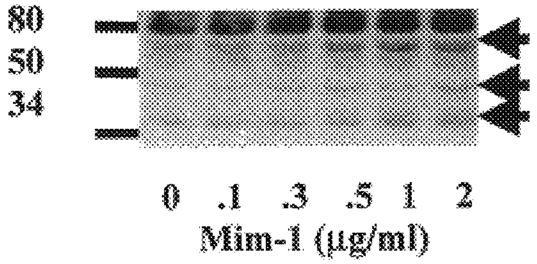
FIG. 9 shows the effect of purified mim-1 on tyrosine phosphorylation in mesenchymal cells. Cells were treated with the indicated concentrations of mim-1 for 3 minutes, washed, lysed and 25 $\mu$g protein was resolved on 10% SDS PAGE. Protein was transferred to PVDF membrane and the membranes probed with phosphotyrosine antibody (4G10 clone; United Biotechnology Incorporated) diluted 1:1000. Data are representative of three separate experiments.
Figure 10:
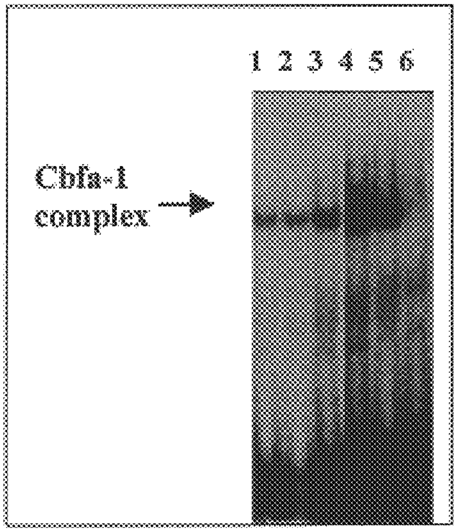
FIG. 10 shows the effect of mim-1 treatment on cbfal binding to osteocalcin promoter binding site. Osteocalcin is a late marker in osteoblast differentiation. MG63 cells were treated with 2 $\mu$g/ml of purified mim-1 for 0, 10, 30, 120 or 240 minute (lanes 1–5), washed, lysed and nuclear extracts prepared. A double stranded 27 bp oligonucleotide from the osteocalcin proximal cbfal binding site was 5' end labeled with $\gamma^{32}$P-ATP by T4 kinase. Equivalent amounts of nuclear extracts were incubated with the probe for 30 min and samples were resolved on 5% SDS PAGE gels, fixed, dried and binding detected by autoradiography. Lane 6 is 120 min treatment (compare to lane 4) in the presence of 100 fold excess unlabeled oligonucleotide included to demonstrate specificity of binding. The dye front on the left of the gel ran slightly faster than the right, accounting for the difference in intensity of the free probe. The data is representative of two separate experiments.

The role of mim-1 in modulating signal transduction in osteoblast precursor cells was examined as follows. Mim-1 stimulated increased tyrosine phosphorylation of proteins ranging in molecular weight from 40 to 80 kDa (FIG. 9), including activation of MAP kinase. Furthermore, mim-1 stimulated a five-fold increase in binding of the osteoblast specific transcription factor, cbfal, to the osteocalcin promoter in electrophoretic mobility shift assays (FIG. 10). Osteocalcin is a marker of late osteoblast differentiation, and the data strongly suggest that mim-1 stimulates differentiation of osteoblastic precursor cells.

Regulation of bone mass is a complex process requiring tight regulation of the cellular activity of both osteoclasts and osteoblasts. This tight regulation necessitates an intricate and dynamic coordination of cellular signals. It has long been speculated that a wide variety of molecules including neuropeptides (29), IL-6 (30), osteoprotegrin (7, 31), parathyroid hormone (32), TGFβ (33), prostaglandins (34) and osteopontin (35), to name a few, are important mediators of cellular signaling between osteoclasts and osteoblasts. Much attention has also been focused on signaling between osteoblasts and osteoclasts (13, 36, 37).

Many factors are involved in recruiting precursor cells of osteoblast or osteoclast lineage. It would seem especially important for osteoclasts to have a mechanism to stimulate recruitment of osteoblastic precursors. Such a pathway would allow for coordinated remodeling of bone. Secretion of an abundant cellular protein which is important in maintaining the balance between bone degradation and bone synthesis has not been reported in either osteoblasts or osteoclasts. Secretion of an abundant osteoclastic protein may be necessary to attain physiologically relevant concentrations of a 35 kDa protein in the bone microenvironment.

A 35 kDa osteoclast protein, mim-1, was unambiguously identified that was secreted in a time dependent manner. Mim-1 secretion was correlated with increased osteoclast activity when stimulated by PMA (FIG. 3). Mim-1 was originally cloned from chicken marrow promyelocytes (15). In these cells mim-1 was very abundant, consistent with the observation in osteoclasts. There is no known function described for mim-1 (15) and thus its potential role in osteoclast or osteoblast biology is not readily apparent. However, mim-1 and a 16 kD protein (Lect2) that has sequence homology with mim-1 are both reported to be secreted proteins (15, 38, 39). Interestingly, Lect2 (also known as chondromodulin II (40)) has chemokine activity in attracting neutrophils (38, 39) and stimulates osteoblast proliferation (41). Mim-1 was speculated to have some function in the milieu of bone marrow, or to possibly serve as a structural protein in granules where it is localized (15).

Figure 4:
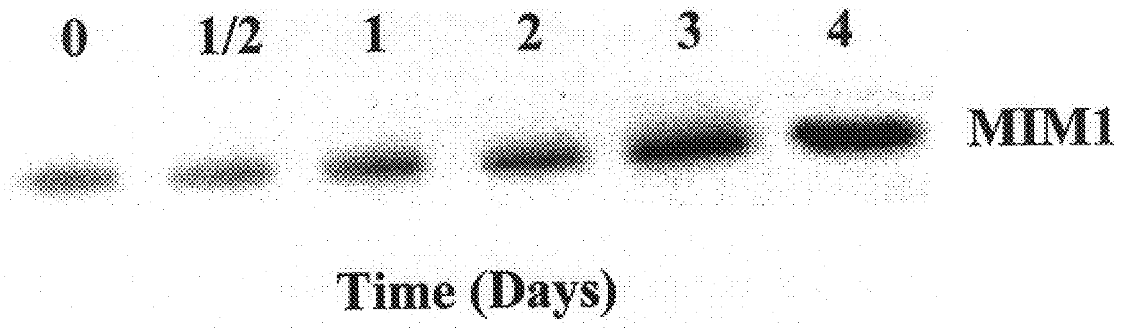
FIG. 4 shows that osteoclasts secrete mim-1 in a time dependent manner. Osteoclasts were cultured as described above in the absence of PMA and aliquots of media removed at the indicated times, samples were resolved on 10% SDS-PAGE, transferred to PVDF membrane and the level of mim-1 determined by Western analysis. Data is from a single experiment performed in duplicate.
Figure 5:
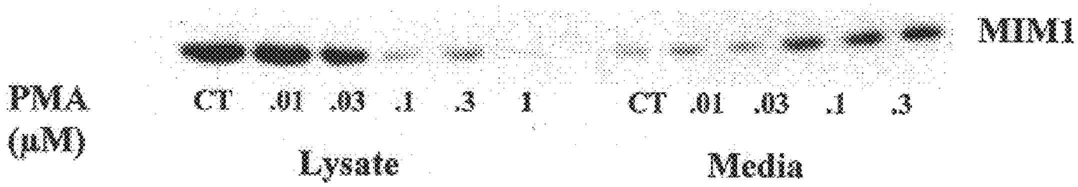
FIG. 5 shows the PMA concentration-dependent secretion of mim-1 by osteoclasts. Avian osteoclasts were cultured in the presence of increasing concentrations of PMA for 4 days; cells were washed with ice cold PBS and lysed. Culture media was collected from each treatment and boiled in sample buffer. Protein (25 $\mu$g) from cell lysates (Lysates) and equal aliquots of the corresponding media (Media) were resolved on 10% SDS-PAGE, transferred to PVDF membrane and Western blotted for mim-1. Molecular weights (kilodaltons) are indicated on the left. Representative of n=2 separate experiments.

The present data indicates that mim-1 was secreted by isolated osteoclasts under basal conditions since mim-1 accumulated in media over a four day incubation in culture (FIG. 4). However, mim-1 secretion was rapidly increased in response to PMA treatment of osteoclasts (FIG. 5). The PMA concentration dependent increase in bone resorption is paralleled by an increase in calmodulin protein levels, and calmodulin antagonists inhibit both the PMA dependent increase in bone resorption and calmodulin levels. In contrast, the calmodulin antagonists did not inhibit the secretion of mim-1.

Analysis of mim-1 sequence demonstrates two imperfect direct repeat sequences of 136 amino acids linked together by a 14 amino acid tether. In the 136 amino acid repeat sequences only 30 amino acids are non-identical (77% identity) and most of the 30 non-identical sites have conservative substitutions. Lect2/chondromodulin II (38, 39) has high sequence homology with the repeat structure in mim-1 but is a 16 kD protein isolated from human T-cells. Lect2 is expressed primarily in liver and is a distinct gene product from mim-1 (40).

The majority of previous investigations of the mim-1 protein involved transcriptional regulation of mim-1 gene expression (15). Northern blot analysis indicated that bone marrow was the tissue with the only detectable expression of mim-1 and that mim-1 was localized in promyelocytes but was not expressed in brain, heart, lung, kidney, liver, muscle, thymus, bursa or spleen (15). Transcriptional regulation of mim-1 expression is governed by the transcription factor myb. Myb activity in regulating mim-1 expression is reported to undergo synergistic activation with C/EBP (42, 43). Interestingly, transcriptional regulation of mim-1 expression is negatively regulated by PU.1 which has been previously been reported to be necessary for osteoclast differentiation (44). In fact PU.1 knockouts are osteopetrotic (43), while neutrophils deficient in PU.1 fail to differentiate (45). In addition, myb knockouts are embryonic lethals due to a failure of hepatic hematopoiesis (46). Furthermore, there is a negative correlation between expression of mim-1 and cell differentiation (15).

Figure 11:
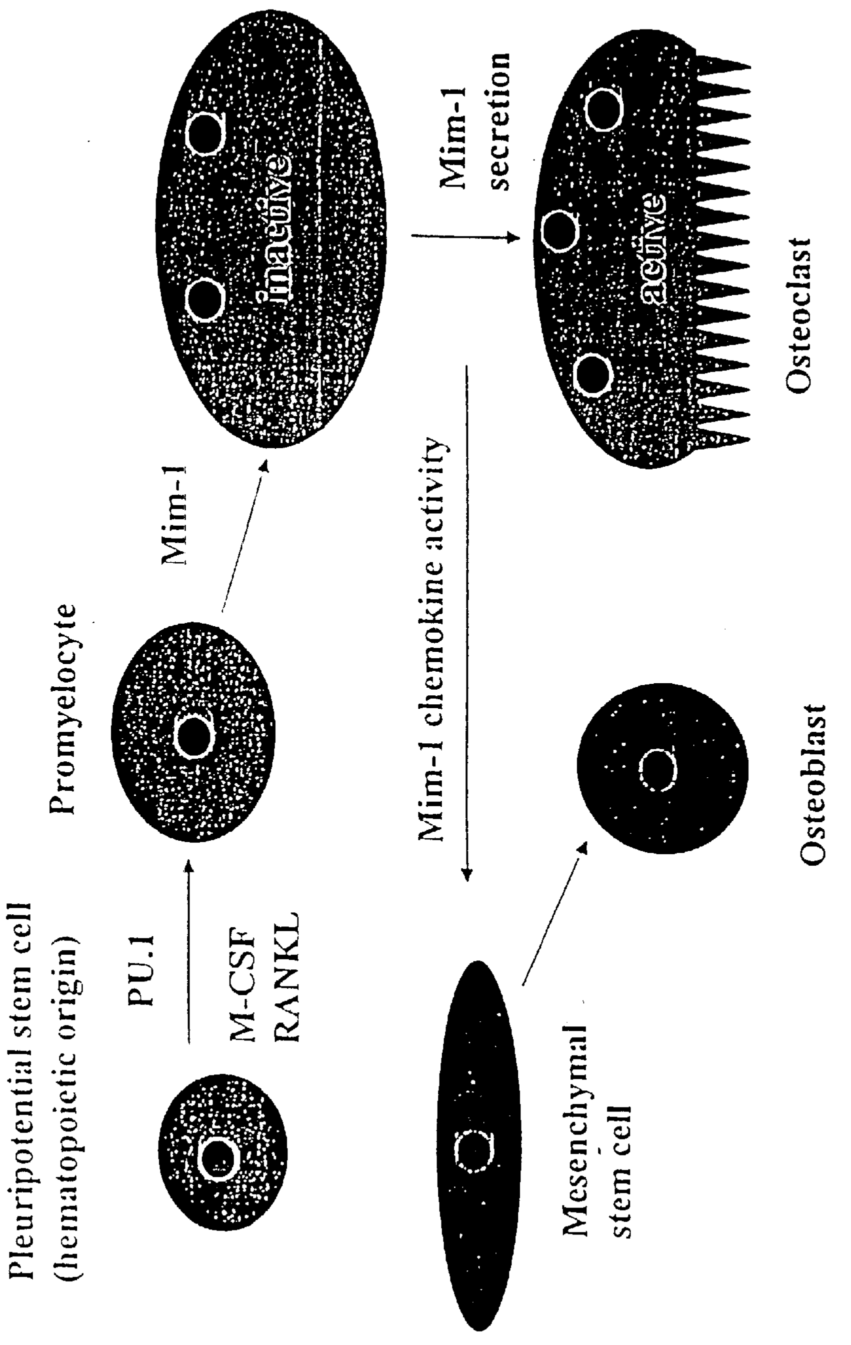
FIG. 11 shows the potential role of mim-1 in bone biology. Osteoclasts are derived from pleuripotential hematopoietic stem cells that express mim-1, while osteoblasts are derived from mesenchymal stem cells that do not express mim-1. Differentiation of osteoclast precursor cells requires RANKL on stromal cells in the presence of M-CSF. Secretion of the abundant mim-1 protein by osteoclasts may results in physiologically relevant concentrations of mim-1 in the bone microenvironment. Mim-1 may be important in regulating differentiation of osteoclast precursors, as well as modulating the recruitment, development and/or activity of osteoblast precursor cells, thus coordinating new bone synthesis in areas of recent bone resorption.

Mim-1 was first identified in promyelocytes and is abundant in freshly isolated osteoclasts (FIGS. 2, 5, and 7), which were reported to be derived from promyelocytes in the presence of stromal cells (47, 48). Together with the fact that mim-1 is secreted preceding a 4-fold stimulation of osteoclastic bone resorption by PMA, these data suggest that mim-1 may have paracrine effects on osteoclast differentiation. In addition, due to the high sequence homology with the neutrophil chemokine Lect2, mim-1 may have a dual purpose in bone. Mim-1 may is also serve to attract osteoblast precursor cells to areas of recent bone resorption, thereby participates in a mechanism of coordinating bone remodeling (FIG. 11).

The following references were cited herein:

1. Suda et al. (1992) Endocrine Rev. 13: 66–68.
2. Fujikawa et al. (1996) Endocrinology 137: 4058–4060.
3. Udagawa et al. (1990) Proc. Natl. Acad. Sci. USA 87:7260–7264.
4. Tanaka et al. (1993) J. Clin. Invest. 91: 257–263.
5. Yasuda et al. (1998) Proc. Natl. Acad. Sci. USA. 95: 3597–3602.
6. Wani et al. (1999) Endocrinology 140:1927–1935.
7. Simonet et al. (1997) Cell 89: 309–319.
8. Wong et al. (1997) J. Biol. Chem. 272: 25190–27194.
9. Horowitz. (1998) J. Clin. Densitometry 1: 187–198.
10. Menaa et al. (1999) J. Clin. Invest. 103: 1605–1613.

11. Ohsaki et al. (1992) Endocrinology 131: 2229–2234.
12. Oursler. (1994) J. Bone Miner. Res. 9: 443–452.
13. Manolagas and Weinstein. (1999) J. Bone Miner. Res. 14: 1061–1066.
14. Fuller et al. (1998) J. Endocrinol. 158:341–350.
15. Ness et al. (1989) Cell 59: 1115–1125.
16. Blair et al. (1986) J. Cell Biol. 102:1164–1172.
17. Williams et al. (1996) J. Biol. Chem. 271:12488–12495.
18. Teitelbaum et al. (1979) Calcif Tissue Int. 27: 255–261.
19. Carano et al. (1993) Am J. Physiol. 264: C694–C701.
20. Dong et al. (1999) J. Cell. Biochem. 73: 478–487.
21. Towbin et al. (1979) Proc. Natl. Acad. Sci. USA 76: 4350–4354.
22. Hellman et al. (1995) Anal. Biochem. 224: 451–455.
23. Jeno et al. (1995) Anal. Biochem. 224: 75–82.
24. Davis and Lee. (1998) J. Am. Soc. Mass Spectrometry 9: 194–201.
25. Moore et al. (1998). Anal. Chem. 70: 4879–4884.
26. Eng et al. (1995) J. Am. Soc. Mass Spectrom. 5: 976–989.
27. Williams et al. (submitted).
28. Williams et al. (1997) Biochem. Biophys. Res. Commun. 235: 646–671.
29. Konttinen et al. (1996) Acta Orthopaedica Scandinavica 67: 632–639.
30. Manolagas. (1998) Annals of the New York Academy of Sciences 840: 194–204.
31. Lacey et al. (1998) Cell 93: 165–176.
32. Partridge et al. (1994) J. Cell. Biochem. 55: 314–327.
33. Duivenvoorden et al. (1999) Clinical & Experimental Metastasis 17: 27–34.
34. Kawaguchi et al. (1995) Clinical Orthopaedic & Related Res. 313: 36–46.
35. Yamata et al. (1997) Endocrinology 138: 3047–3055.
36. Kahn and Partridge. (1987) Am. J. Otolaryngol. 8: 258–264.
37. Aurbach et al. (1985) in Williams' Textbook of Endocrinology (Wilson J D and Foster D W eds.) $7^{th}$ Ed., pp. 1173–1174, WB Saunders Co., Philadelphia.
38. Yamagoe et al. (1997) Biochem. Biophys. Res. Commun. 237: 116–120.
39. Yamagoe et al. (1996) Immunol. Lett. 52: 9–13.
40. Shukunami et al. (1998) J. Biochem. 125: 436–442.
41. Mori et al. (1997) FEBS Letters 406: 310–314.
42. Burk et al. (1993) The EMBO Journal 12: 2027–2038.
43. Oelgeschlager et al. (1996) The EMBO Journal 17: 2771–2780.
44. Tondravi et al. (1997) Nature: 386:81–84.
45. Anderson et al. (1998) Blood 92: 1576–1585.
46. Oh and Reddy. (1999) Oncogene 18: 3017–3033.
47. Nutt et al. (1999). Nature 401: 556–562.
48. Rolink et al. (1999) Nature 401: 603–606.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inducing recruitment and differentiation of osteoblasts, comprising the step of:

administering the myb induced myeloid protein-1 of SEQ ID NO. 8 to said osteoblasts, wherein said administering induces said recruitment and differentiation.

2. A method of inducing recruitment and differentiation of osteoblasts, comprising the step of:

administering a fragment of the myb induced myeloid protein-1 of SEQ ID NO. 8 to said osteoblasts, wherein said fragment has the activity of inducing recruitment and differentiation of osteoblasts, or administering a fusion protein containing said fragment, wherein said administering induces said recruitment and differentiation.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Gallus gallus
<220> FEATURE:
<222> LOCATION: 200..209
<223> OTHER INFORMATION: amino acid sequence tryptic peptide from
      mim-1 protein

<400> SEQUENCE: 1

      Tyr Gly Cys Gly Tyr Phe Gly Ala Pro Arg
                      5                   10


<210> SEQ ID NO 2
<211> LENGTH: 8
<212> TYPE: PRT
<213> ORGANISM: Gallus gallus
<220> FEATURE:
<222> LOCATION: 116..123
<223> OTHER INFORMATION: amino acid sequence tryptic peptide from
      mim-1 protein

<400> SEQUENCE: 2

      Leu Val Cys Ile His Pro Ile Arg
                      5
```

-continued

```
<210> SEQ ID NO 3
<211> LENGTH: 15
<212> TYPE: PRT
<213> ORGANISM: Gallus gallus
<220> FEATURE:
<222> LOCATION: 94..108
<223> OTHER INFORMATION: amino acid sequence tryptic peptide from
      mim-1 protein

<400> SEQUENCE: 3

      Phe Phe His Asn Gly Asn Ser Ile Asp Asp Gly Val Gln Ile Arg
                       5                  10                  15


<210> SEQ ID NO 4
<211> LENGTH: 8
<212> TYPE: PRT
<213> ORGANISM: Gallus gallus
<220> FEATURE:
<222> LOCATION: 266..273
<223> OTHER INFORMATION: amino acid sequence tryptic peptide from
      mim-1 protein

<400> SEQUENCE: 4

      Leu Leu Cys Ile His Pro Ile Arg
                       5


<210> SEQ ID NO 5
<211> LENGTH: 22
<212> TYPE: PRT
<213> ORGANISM: Gallus gallus
<220> FEATURE:
<222> LOCATION: 94..115
<223> OTHER INFORMATION: amino acid sequence tryptic peptide from
      mim-1 protein

<400> SEQUENCE: 5

      Phe Phe His Asn Gly Asn Ala Ile Asp Asp Gly Val Gln Ile Ser
                       5                  10                  15
      Gly Ser Gly Tyr Cys Val Lys
                      20


<210> SEQ ID NO 6
<211> LENGTH: 16
<212> TYPE: PRT
<213> ORGANISM: Gallus gallus
<220> FEATURE:
<222> LOCATION: 293..308
<223> OTHER INFORMATION: amino acid sequence tryptic peptide from
      mim-1 protein

<400> SEQUENCE: 6

      Val Phe Pro Gly Ile Ile Ser His Ile His Val Glu Asn Cys Asp
                       5                  10                  15
      Arg


<210> SEQ ID NO 7
<211> LENGTH: 25
<212> TYPE: PRT
<213> ORGANISM: Gallus gallus
<220> FEATURE:
<222> LOCATION: 219..243
<223> OTHER INFORMATION: amino acid sequence tryptic peptide from
      mim-1 protein

<400> SEQUENCE: 7

      Gly Val Asp Val Ile Cys Ala Asp Gly Ala Thr Val Tyr Ala Pro
                       5                  10                  15
      Phe Ser Gly Glu Leu Ser Gly Pro Val Lys
                      20                  25
```

-continued

```
<210> SEQ ID NO 8
<211> LENGTH: 326
<212> TYPE: PRT
<213> ORGANISM: Gallus gallus
<220> FEATURE:
<223> OTHER INFORMATION: amino acid sequence of mim-1 protein

<400> SEQUENCE: 8

      Met Pro Ala Leu Ser Leu Ile Ala Leu Leu Ser Leu Val Ser Thr
                      5                   10                  15
      Ala Phe Ala Arg Gln Trp Glu Val His Pro Pro Gln Gln Gln Gly
                      20                  25                  30
      Arg His Trp Ala Gln Ile Cys Ser Gly Asn Pro Phe Asn Arg Ile
                      35                  40                  45
      Arg Gly Cys Asp Arg Tyr Gly Cys Gly Asn Tyr Gly Ala Ser Arg
                      50                  55                  60
      Gln Gly Lys Gly Glu Lys His Lys Gly Val Asp Val Ile Cys Thr
                      65                  70                  75
      Asp Gly Ser Ile Val Tyr Ala Pro Phe Trp Gly Gln Leu Ser Gly
                      80                  85                  90
      Pro Ile Arg Phe Phe His Asn Gly Asn Ala Ile Asp Asp Gly Val
                      95                  100                 105
      Gln Ile Ser Gly Ser Gly Tyr Cys Val Lys Leu Val Cys Ile His
                      110                 115                 120
      Pro Ile Arg Tyr His Gly Gln Ile Gln Lys Gly Gln Gln Leu Gly
                      125                 130                 135
      Arg Met Leu Pro Met Gln Lys Val Phe Pro Gly Ile Val Ser His
                      140                 145                 150
      Ile His Val Glu Asn Cys Asp Gln Ser Asp Pro Thr His Leu Leu
                      155                 160                 165
      Arg Pro Ile Pro Asp Ile Ser Pro Pro Phe Pro Gln Gln Asp Ala
                      170                 175                 180
      His Trp Ala Val Val Cys Ala Gly Asn Pro Thr Asn Glu Ile Arg
                      185                 190                 195
      Gly Cys Lys Asp Tyr Gly Cys Gly Tyr Phe Gly Ala Pro Arg Arg
                      200                 205                 210
      Asn Gly Lys Gly Glu Lys His Lys Gly Val Asp Val Ile Cys Ala
                      215                 220                 225
      Asp Gly Ala Thr Val Tyr Ala Pro Phe Ser Gly Glu Leu Ser Gly
                      230                 235                 240
      Pro Val Lys Phe Phe His Asn Gly Asn Ala Ile Asp Asp Gly Val
                      245                 250                 255
      Gly Ile Arg Gly Ser Gly Phe Cys Val Lys Leu Leu Cys Ile His
                      260                 265                 270
      Pro Ile Arg Tyr Asn Gly Arg Ile Ser Lys Gly Gln Val Leu Gly
                      275                 280                 285
      Arg Met Leu Pro Met Gln Arg Val Phe Pro Gly Ile Ile Ser His
                      290                 295                 300
      Ile His Val Glu Asn Cys Asp Arg Ser Asp Pro Thr Ser Asn Leu
                      305                 310                 315
      Glu Arg Gly Lys Gly Glu Ser Glu Met Glu Val
                      320                 325


<210> SEQ ID NO 9
<211> LENGTH: 113
<212> TYPE: PRT
<213> ORGANISM: unknown
<220> FEATURE:
<222> LOCATION: 38..165
<223> OTHER INFORMATION: amino acid sequence of region of Lect2
      protein homologous to repeat sequences of N
      and C terminal ends of the mim-1 protein

<400> SEQUENCE: 9

      Tyr Gly Cys Gly Gln Tyr Ser Ala Gln Arg Thr Gln Arg His His
                      5                   10                  15
      Pro Gly Val Asp Val Leu Cys Ser Asp Gly Ser Val Val Tyr Ala
                      20                  25                  30
      Pro Phe Thr Gly Lys Ile Val Gly Gln Glu Lys Pro Tyr Arg Asn
                      35                  40                  45
      Lys Asn Ala Ile Asn Asp Gly Ile Arg Leu Ser Gly Arg Gly Phe
                      50                  55                  60
      Cys Val Lys Ile Phe Tyr Ile Lys Pro Ile Lys Tyr Lys Gly Ser
                      65                  70                  75
      Ile Lys Lys Gly Glu Lys Leu Gly Thr Leu Leu Pro Leu Gln Lys
```

-continued

```
                 80                  85                  90
Ile Tyr Pro Gly Ile Gln Ser His Val His Val Glu Asn Cys Asp
                 95                  100                 105
Ser Ser Asp Pro Thr Ala Tyr Leu
                 110
```

```
<210> SEQ ID NO 10
<211> LENGTH: 115
<212> TYPE: PRT
<213> ORGANISM: Gallus gallus
<220> FEATURE:
<222> LOCATION: 51..165
<223> OTHER INFORMATION: amino acid sequence of repeat sequence of N
      terminal end of mim-1 protein homologous
      to Lect2 protein

<400> SEQUENCE: 10

Tyr Gly Cys Gly Asn Tyr Gly Ala Ser Arg Gln Gly Lys Gly Glu
                 5                   10                  15
Lys His Lys Gly Val Asp Val Ile Cys Thr Asp Gly Ser Ile Val
                 20                  25                  30
Thr Ala Pro Phe Ser Gly Gln Leu Ser Gly Pro Ile Arg Phe Phe
                 35                  40                  45
His Asn Gly Asn Ala Ile Asp Asp Gly Val Gln Ile Ser Gly Ser
                 50                  55                  60
Gly Phe Cys Val Lys Leu Leu Cys Ile His Pro Ile Arg Tyr Asn
                 65                  70                  75
Gly Arg Ile Ser Lys Gly Gln Val Leu Gly Arg Met Leu Pro Met
                 80                  85                  90
Gln Arg Val Phe Pro Gly Ile Ile Ser His Ile His Val Glu Asn
                 95                  100                 105
Cys Asp Arg Ser Asp Pro Thr Ser Asn Leu
                 110                 115
```

```
<210> SEQ ID NO 11
<211> LENGTH: 115
<212> TYPE: PRT
<213> ORGANISM: Gallus gallus
<220> FEATURE:
<222> LOCATION: 200..315
<223> OTHER INFORMATION: amino acid sequence of repeat sequence of C
      terminal end of mim-1 protein homologous
      to Lect2 protein

<400> SEQUENCE: 11

Thr Gly Cys Gly Tyr Phe Gly Ala Pro Arg Asn Gly Lys Gly Glu
                 5                   10                  15
Lys His Lys Gly Val Asp Val Ile Cys Ala Asp Gly Ala Thr Val
                 20                  25                  30
Tyr Ala Pro Phe Ser Gly Glu Leu Ser Gly Pro Val Lys Phe Phe
                 35                  40                  45
His Asn Gly Asn Ala Ile Asp Asp Gly Val Gln Ile Arg Gly Ser
                 50                  55                  60
Gly Tyr Cys Val Lys Leu Val Cys Ile His Pro Ile Arg Tyr His
                 65                  70                  75
Gly Gln Ile Gln Lys Gly Gln Gln Leu Gly Arg Met Leu Pro Met
                 80                  85                  90
Gln Lys Val Phe Pro Gly Ile Val Ser His Ile His Val Glu Asn
                 95                  100                 105
Cys Asp Gln Ser Asp Pro Thr His Leu Leu
                 110                 115
```